United States Patent [19]

Antonucci et al.

[11] Patent Number: 5,498,643
[45] Date of Patent: Mar. 12, 1996

[54] METHOD AND COMPOSITION FOR PROMOTING IMPROVED ADHESION TO SUBSTRATES

[75] Inventors: Joseph M. Antonucci, Kensington; Patricia A. Bennett, Germantown, both of Md.

[73] Assignee: The United States of America as represented by the Secretary of Commerce, Washington, D.C.

[21] Appl. No.: 189,709

[22] Filed: Feb. 1, 1994

[51] Int. Cl.$^6$ .............................. A61K 6/08; A61C 5/00
[52] U.S. Cl. .................. 523/118; 523/116; 433/228.1; 106/35; 526/217
[58] Field of Search .................................. 523/114, 115, 523/116, 118; 524/812; 433/228.1; 526/90, 123, 217

[56] References Cited

U.S. PATENT DOCUMENTS

| | | | |
|---|---|---|---|
| 4,514,527 | 4/1985 | Bowen | 523/115 |
| 4,521,550 | 6/1985 | Bowen | 523/116 |
| 4,588,756 | 5/1986 | Bowen | 523/116 |
| 4,659,751 | 4/1987 | Bowen | 523/116 |
| 4,732,887 | 3/1988 | Obanawa et al. | 502/402 |
| 5,270,351 | 12/1993 | Bowen | 523/115 |
| 5,320,886 | 6/1994 | Bowen | 523/116 |
| 5,364,890 | 11/1994 | Sakima et al. | 523/118 |

FOREIGN PATENT DOCUMENTS

| | | |
|---|---|---|
| 0284275A1 | 9/1988 | European Pat. Off. |
| WO94/00096 | 1/1994 | WIPO |

OTHER PUBLICATIONS

Search Report From International Stage of PCT/US95/01063.

Bowen et al., "Development of an Adhesive System for Bonding to Hard Tooth Tissues", Journal of Esthetic Dentistry, vol. 3, pp. 86–90 (1991).

Webb et al., "Dentin–bonding Efficiency Using N–Phenylglycine, N–Phenyl–beta–Alanine, or N–Methyl–N–Phenylglycine", Journal of Dental Research, pp. 211–214 (1991).

Bowen et al., "Development of an Adhesive Bonding System", Operative Dentistry, Suppl. 5, pp. 75–80 (1992).

Schumacher et al., "Effects of Surface–active Resins on Dentin/Composite Bonds", Dent Mater 8, pp. 278–282 (1992).

Bowen et al., "Adhesion of Composites to Dentin and Enamel", CDA Journal, pp. 19–22 (1993).

Miniotis et al., "Molar Efficiency Study of Chlorinated NPG Substitutes in Dentin Bonding", Journal of Dental Research, vol. 72, pp. 1045–1049 (1993).

Frederick C. Eichmiller, "A Clinical Perspective on Dentin Adhesives", IDA Journal, Resources 4, pp. 22–24 (1993).

*Primary Examiner*—Tae Yoon
*Attorney, Agent, or Firm*—Leydig, Voit & Mayer, Ltd.

[57] ABSTRACT

An etchant/primer composition is provided which includes (a) a compound having the formula $$RN(CH_2YCO_2M)_2 \qquad (I)$$

wherein $R=R^1$ or $R^2$;
  $R^1$=an aromatic group;
  $R^2$=a conjugated aliphatic group;
  Y=a single bond, $CH_2$, $CHCH_3$ or $C=CH_2$; and
each M is independently H, an alkali metal, an alkaline earth metal, aluminum, a transition or redox metal or an alkyl group having 1 to 18 carbon atoms, with the proviso that when both M groups are alkyl groups, the compound corresponding to formula I be capable of being easily hydrolyzed, displaced or exchanged with other reagents present in the etchant/primer composition and (b) a polar solvent system. An etchant/primer/adhesive monomer composition is also provided which includes the etchant/primer composition and an adhesive monomer system. One and two step simplified methods for adhering and for preparing a substrate surface, such as a dental substrate surface, to a polymeric material are also provided. Kits which may be used with these compositions and methods are also provided.

25 Claims, 2 Drawing Sheets

METHOD AND COMPOSITION FOR PROMOTING IMPROVED ADHESION TO SUBSTRATES

BACKGROUND OF THE INVENTION

1. Field of the Invention

The present invention is directed to a composition for and methods of improving adhesion of conventional adhesives to substrates. More particularly, the present invention is directed to methods and compositions for the improvement of adhesive bonding of acrylic resins to substrates found in industrial, natural and dental environments, such as those involved in dental restorations and for protective sealants.

2. Description of Related Art

The ability to form strong, durable bonds between restorative or sealant materials and skeletal tissue, such as bone and tooth structure, has a number of important advantages. Effective adhesives for such purposes, particularly dental adhesives, provide a means of bonding that does not require the removal of healthy dental tissue, e.g., by eliminating the need for mechanical undercuts for retention of restorations. In addition, the use of dental adhesives can eliminate microleakage at the restorative-tooth interface, which, if unresolved, can lead to gap formation, margin discoloration, sensitivity, and the potential formation of secondary caries. In addition, dental adhesives improve the stress distribution at the tooth-restoration interface and can reinforce decay-weakened tooth structures. Adhesives are also capable of enhancing the bonding of protective sealant materials to tooth structure, especially to dental tissue that is not amenable to acid etching, a method which has been used in some situations heretofore but which has certain attendant detrimental effects. A wider application of conservative and preventive dental practices thus depends on the availability of effective dental adhesive systems.

A major shortcoming of polymer-based restoratives and sealants, as well as other types of materials, is their inherent inability to adhere to enamel and, particularly, dentin. Adequate adhesion to enamel, in most situations, can be achieved by acid etch techniques that employ aqueous solutions of inorganic or organic acids, such as phosphoric, nitric, citric, maleic acids, etc. These techniques enable dental resins to infiltrate the microporous surface of the etched enamel and form interlocking polymeric tags. Forming bonds of suitable strength to dentin, which is a vital, more complex, heterogeneous substrate than enamel, has only recently been achieved. As currently practiced, bonding to dentin involves a number of steps, usually including a dentin conditioner or etchant, that alters the surface of the dentin. This etchant has typically been an acidic solution similar to, but usually more dilute than, those employed with enamel. The cleansed dentin surface is then conditioned further with a surface-active compound referred to as a "primer", commonly in solution, and finally treated with an adhesion-promoting monomer (also commonly used in solution) that can diffuse and polymerize in the conditioned dentin to form a resin-impregnated interface or hybrid layer.

As indicated above, currently used dentin bonding systems generally include 3 basic components: (1) a dentin conditioner, (2) a dentin primer, and (3) a resin-based bonding agent or polymer-forming monomer(s). Dentin conditioners are generally aqueous solutions of inorganic or organic acidic agents, such as phosphoric, nitric, citric, maleic acids, etc. Some conditioners employ chelating compounds, based on ethylenediaminetetraacetic acid (EDTA), which are also applied to dentin in the form of aqueous solutions. The function of the dentin conditioner is to remove or alter what is known as the "smear layer" a coating of debris that forms on the dentin surface as a result of the cutting and grinding processes of cavity preparation. Application of the dentin conditioner is regarded as a critical step in establishing effective bonding to dentin as this makes it possible for the other components of the dentin adhesive system to wet, infiltrate or penetrate, and conform to the heterogeneous, vital dentinal substrate.

Primers are surface-active compounds that exhibit both an affinity for dentin and adhesive resin systems and participate in the polymerization process, thereby promoting adhesion between the primarily hydrophilic dentin and the predominantly hydrophobic polymeric adhesives or monomers from which they are formed. Primers are applied to dentin in solution form, such as acetone, ethanol, monomeric solutions, water and various mixed solvent systems. A widely used primer is N-phenylglycine (NPG), which, in addition to its surface-active properties, also functions as a co-initiator or activator during interfacial polymerization.

The bonding resins or monomers used to form the bonding adhesives are generally simple acrylic monomers such as methyl methacrylate, 2,2-bis[p-( 2'-hydroxy-3'-methacryloxypropoxy)phenyl]propane (Bis-GMA), triethylene glycol dimethacrylate, 2-hydroxyethyl methacrylate, etc., as well as various monomeric combinations (monomer systems). Especially effective monomeric bonding agents are those that have surface-active functional groups, e.g., carboxylic acid, carboxylic acid anhydride, phosphate, sulfonate, sulfinate, aldehyde, isocyanate, hydroxyl, amide, etc. A particularly effective surface-active monomer is the reaction product of 2-hydroxyethyl methacrylate and pyromellitic acid dianhydride (PMDM). In addition to the above components, dentin adhesive systems incorporate chemical, photochemical and dual-curing free-radical initiators. Bonding systems which have proven fairly useful in recent years include a number described by Rafael L. Bowen in several of his U.S. Pat. Nos.: 4,514,527; 4,521,550; 4,588,756; 4,659,751 and 5,270,351. These patents disclose a bonding procedure for achieving adhesion to tooth structures and other substrates that involve the use of an acid, such as nitric acid, for removing the smear layer, the use of an N-aryl-$\alpha$-amino acid such as N-phenylglycine to prime the surface and the application of a surface-active monomer such as PMDM.

Some of these bonding systems are characterized by the ability to undergo a self-initiated interfacial polymerization and are especially effective for bonding to dentin. For example, the sequential application of a dilute aqueous nitric acid solution as the etchant, N-phenylglycine (NPG) in acetone as the primer, and an acetone solution of a carboxylic acid-containing monomer, PMDM, has been shown to yield strong composite-to-dentin bonding. In this system, effective interfacial free-radical polymerization is initiated by the interaction of PMDM with the infused NPG. A number of other N-aryl-$\alpha$-amino acids have been used as primers in place of NPG, and a variety of carboxylic acid monomers have been substituted for PMDM in this bonding system in attempts to further enhance the efficiency of this type of bonding system. The procedures described, however, require the use of separate etchant and primer steps to prepare and predispose the dentin surface for bonding to resin-based dental materials.

Although current dentin adhesive systems such as the aforementioned, show considerable improvement over their earlier versions, they are still far from ideal. Current systems

3 have complex compositions and application protocols which make dentin bonding an extremely technique-sensitive dental procedure.

SUMMARY OF THE INVENTION

An object of this invention is a more effective, simpler dentin bonding system based on the use of a special type of unsaturated amino acid. Another object of the present invention is providing a bonding system that includes a single composition dentin conditioner or etchant and a dentin primer. Yet another object of the present invention is the provision of a bonding system that includes both self-etching and radical-initiating properties in a single chemical agent.

The present invention is directed to a simple, effective method for bonding, preferably to mineralized dental tissue, such as enamel and dentin, which requires fewer steps, is less technique-sensitive than prior procedures, by virtue of less complex compositions and application protocols.

The present invention is directed to a composition suitable for preparing a substrate, such as skeletal tissue, particularly a tooth surface and most particularly, dentin, for subsequent adhesive bonding thereto. The compositions provide both a conditioning and priming function. In addition, these compositions provide self-etching and radical-initiating properties such that they eliminate the need for the use of a separate dentin conditioner and a primer and in many instances eliminate the need for a separate polymerization initiator and/or activator. Thus, the same composition may serve the dual functions of etchant and primer, and in many situations, may serve as a combined etchant, primer and initiator. The use of the methods according to the present invention reduces what is typically a 3 or 4 step procedure of preparing for and applying an adhesive used for preparing enamel and, particularly, dentin surfaces in current dental practice to a simple 1 or 2 step procedure.

The agent employed in the compositions of the present invention, a preferred type of amino acid, described below, has the ability in aqueous or water-containing solutions to both cleanse and activate a substrate surface, for example the surface of dentin, in a single step for subsequent bonding to resin-based materials. The agent employed in these compositions is a derivative of iminodiacetic acid and salts thereof. The "conditioning" and "priming" (or cleansing and activating) agent of the present invention has the general formula:

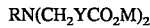     (I)

wherein $R=R^1$ or $R^2$;
$R^1$=an aromatic group;
$R^2$=a conjugated aliphatic group;
Y=a single bond, $CH_2$, $CHCH_3$ or $C=CH_2$; and
each M is independently H, an alkali metal, an alkaline earth metal, aluminum, a transition or redox metal or an alkyl group having 1 to 18 carbon atoms, with the proviso that when both M groups are alkyl groups, the compound corresponding to formula I be capable of being easily hydrolyzed or displaced with other reagents present in the etchant/primer composition.

These agents are dissolved in water or other polar solvents or mixed aqueous solvents, for example, low molecular weight ketones, such as acetone, or alcohols, such as ethanol and aqueous solutions thereof.

The present invention also includes two component kits including the aforementioned amino acid etchant and primer agent and an appropriate monomer system, each in an appropriate solvent.

It may be noted that the multi-step bonding protocols, typical of current commercial adhesive systems, generally tend to be a source of material waste and unreasonable technique sensitivity. The amino acid etchant/primer agents of the present invention not only reduce the number of steps normally involved in preparing a substrate surface and applying the adhesive monomer system thereto from 3 or 4 steps to 1 or 2 steps, but less waste and improved restorative or sealant results are obtained. Thus, although conventional aggressive etchants are effective in cleaning the surface of dentin for improved wetting by and diffusion of the components of the adhesive system, they can also weaken the underlying sound dentin by excessive demineralization and disruption of collagen fibrils. These types of etchants typically require an aqueous rinse step to remove residual acid and soluble by-products. Also, the depth of demineralized altered dentin resulting from the use of aggressive etchants may exceed the depth to which an adhesive resin can penetrate the dentin, resulting in a weakened, partially reinforced hybrid dentin zone, and thereby become vulnerable to failure. In contrast, the amino acid agents and solvent systems of the present invention are milder and may be used as single step etchant and primer compositions without subsequent rinsing since they are also effective in the presence of water and/or aqueous solvents. Furthermore, these amino acids demonstrate the ability to act as a free-radical initiator(s) for the types of adhesive monomer systems currently used as dental adhesives. Accordingly, while an aqueous rinse step, such as the type used with multi-step systems to remove residual acid and soluble by-products, may be used, it is unnecessary to employ such a rinse step. In addition, since the amino acid etchant/primer agents of the present invention are effective as free-radical initiators, they may, in fact, be combined with the adhesive monomer system immediately prior to application.

Several methods based on the properties of the etchant/primer compositions of the present invention provide for the preparation of a substrate surface, such as a dentin surface, for subsequent adhesion thereto, one of the methods including the formation of an adhesive bond thereto. Thus, one embodiment involves contacting the substrate surface with the etchant/primer composition of the present invention. Thereafter, either with or without a rinsing step with water, a conventional adhesive composition, typically including a free-radical initiator, may be applied thereto. After subsequent curing, a strong adhesive bond to the substrate is obtained. Such a method involves 2 basic steps, not including a rinsing step.

A strong adhesive bond to a substrate, such as dentin, may also be achieved according to another embodiment of the present invention in a single step. Thus, since the etchant/primer compositions of the present invention function not only to cleanse and condition the surface of a substrate, to a depth from about 1 to 5 microns, but also function as an initiator, for most adhesive monomers used to form an adhesive bond to a substrate surface, such as a dentin surface, it is unnecessary to include a separate initiator or accelerator. Accordingly, the etchant/primer composition of the present invention may be combined with an adhesive monomer system to form an etchant/primer/adhesive monomer system in a single composition. With this embodiment, rather than the 3 or 4 steps typically used to etch, prime and form an adhesive bond to a substrate surface, the etchant/primer/adhesive monomer system may be applied to the substrate by combining an etchant/primer composition according to the present invention with an adhesive monomer system immediately prior to use. By this method, using a single composition in a single step, a strong adhesive bond may be formed to the substrate surface after polymerization (curing) occurs.

DESCRIPTION OF THE PREFERRED EMBODIMENTS

Etchant/Primer Compositions

Figure 1:
FIG. 1 is a scanning electron photomicrograph of freshly cut dentin after a water rinse at 3,000X magnification.

The etchant/primer compositions of the present invention combine a particular type of amino acid in a polar solvent system to provide unique cleaning, etching, activating and coinitiating effects for adhesive monomer systems. In aqueous or other polar solvent systems, these compounds effectively remove interfering debris from dentin surfaces, as well as prime such surfaces for bonding to dental resins by a variety of polymerization modes. These compositions also provide versatile activating/coinitiating, and in some situations, accelerator functions for the polymerization of known adhesive monomer systems used as dental resins. By themselves, and in conjunction with acidic monomers, such as PMDM, they can initiate the polymerization of adhesive monomer systems typically used as dental resins on the dentinal surface. These specific amino acid compounds also function as polymerization accelerators for diacyl peroxides (e.g., benzoyl peroxide) and peroxyesters (e.g., t-butylperoxymaleic acid). They are also effective as photoinitiator/coactivators with vicinal carbonyl compounds, especially diketones, such as camphorquinone. Since bonding to dentin using one or more of these modes of initiation from dentinal surfaces is feasible, these amino acid-based adhesives can be used in a wide range of applications, including situations that are not amenable to photo-polymerization.

Etchant/Primer Compounds

Suitable for use as the etchant/primer compounds of the present invention are derivatives of aminodiacetic acid and salts thereof. When used in dental applications, it is expected that the etchant/primer compounds of the present invention would be used at relatively low concentrations and in small amounts. Nevertheless, the compounds employed are preferred to have a relatively low toxicity. In addition, the compounds in their acidic or salt form should be at least partially soluble in water and completely soluble in the mixed aqueous solvent systems employed. Solubility parameters of the salts of the iminodiacetic acids are preferably similar to those of the monomers employed.

Specifically, compounds having the following formula (I) are suitable:

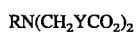  (I)

wherein R=R¹ or R²;

R¹=an aromatic group;
R²=a conjugated aliphatic group;
Y=a single bond, $CH_2$, $CHCH_3$ or $C=CH_2$; and
each M is independently H, an alkali metal, an alkaline earth metal, aluminum, a transition metal or an alkyl group having 1 to 18 carbon atoms, with the proviso that when both M groups are alkyl groups, the compound corresponding to formula I be capable of being easily hydrolyzed or displaced with other reagents present in the etchant/primer composition. An example of an easily hydrolyzed group is t-butyl.

While $R^1$ may be a heterocyclic aromatic group, preferably it is a carbocyclic aromatic group, particularly a phenyl or naphthyl group or derivatives thereof. Most preferred are substituted and unsubstituted phenyl groups. When substituted, the substituents may be at either the ortho, meta or para position of the phenyl group. However, when the substituent is of sufficient size to impart steric hindrance, or is an electron withdrawing group, it is preferred that the substituent be located at the meta- or para- position. Preferred as substituents are groups which are the same as or similar to the iminodiacetic acid group or derivatives thereof, and/or which extend the conjugated system of the aromatic ring.

In the present invention, $R^1$ is preferably $C_6H_5$ or $C_6H_4R^3$,
wherein $R^3=N(CH_2CO_2M)_2$; $C_6H_4N(CH_2CO_2)_2$; $O(CH_2)_2OC_6H_4N(CH_2CO_2M)_2$; $CH=CH_2$; $CO_2H$; F; Cl; Br; I; OH; SH; (m- or p-)$CH_2C_6H_4$(m- or p-)$CH=CH_2$; $OCOC(R^4)=CH_2$; $NR^4COC(R^4)=CH_2$; $(CH_2)_2OCOC(R^4)=CH_2$; $C_6H_5$; an alkyl group having 1 to 12 carbon atoms, such as $CH_3$, $CH_3CH_2$, $(CH_3)_2CH$, $(CH_3)_3C$; $HOCH_2$; $HOCH_2CH_2$; $R^5_2N$; $R^6O$; $R^6S$; $R^6CO$; $R^7CONH$; $R^7COCO$,
wherein $R^4$=H or $CH_3$;
wherein each $R^5$ is independently H or an alkyl group having 1 to 8 carbon atoms and is preferably $CH_3$, or $C_2H_5$;
wherein $R^6$=an alkyl group having from 1 to 6 carbon atoms, preferably $CH_3$;
wherein $R^7$=an alkyl group having 1 to 6 carbon atoms, preferably $CH_3$ or $C_2H_5$.

Suitable for use are also various urethane derivatives of p-2-hydroxyethylphenyliminodiacetic acid or soluble salts thereof, such as $R^8$(p-NHCOO$(CH_2)_2C_6H_4N)CH_2CO_2M)_2)_2$.

In the present invention, $R^2$ may be an unsaturated cycloaliphatic group or, more preferably, an unsaturated aliphatic group, linear or branched, which includes carbon to carbon and/or carbon to nitrogen conjugated unsaturated bond(s). This conjugation results from interaction of the electron pair on iminodiacetic acid nitrogen atom with the carbon to carbon or carbon to nitrogen unsaturated bond electron pair(s). Within the aliphatic group, may be other atoms, such as nitrogen and oxygen atoms. In addition to hydrocarbon groups, this would also include groups such as ester, ether, amino, imino, and amide groups. The number of carbon atoms present in $R^2$ ranges from 4 to about 20.

Preferably, $R^2$ includes one or more vinyl groups and most preferably includes a residue of crotonate ($CH_3CH=CHCO_2M$) or substituted crotonate group present as the free acid, ester or salt of the type described herein for the iminoacetic acid salts. Preferred crotonate derivatives are those in which bonding to the nitrogen atom of the aminodiacetic group takes place either through carbon atom number 2 or carbon atom number 3 of the crotonate residue, with the latter being most preferred. In such an instance, $R^2$ represents $CH_3C=CHCO_2R^9$. $R^9$ represents M, wherein M has the same meaning as indicated above; a vinyl group or an alkyl group having 1 to 24 carbon atoms, preferably $CH_3$ or $CH_3CH_2$. Other preferred $R^2$ groups include the residue of cinnamic acid, present as the free acid, ester or its salt.

In the present invention, although the free acidic form is generally preferred, in some instances salts of N-substituted aminodiacetic acid are preferred. These include such salts as alkali metal salts, alkaline earth metal salts, transition or redox metal salts and certain group IIIA metal salts, as well as ammonium salts. Examples of suitable metal salts include sodium, potassium, ammonium, silver, gold, calcium, magnesium, strontium, copper, aluminum, iron, titanium, zirconium, yttrium, cerium, and the like. Additionally, organocationic salts, such as oraganoammonium and organophosphonium salts, may be employed. Preferred are the dipotassium and magnesium salts.

The most preferred etchant/primer compound of the present invention is N-phenyliminodiacetic acid (PIDAA) and salts thereof, such as the dipotassium and magnesium salts. While reference is made in the following description to the preferred PIDAA and its salts, the other etchant/primer compounds described herein behave similarly. Other iminodiacetic acids and their salts which are preferred in the present invention include m- or p-vinyl-N-phenyliminodiacetic acid; N-p-acrylphenyliminodiacetic acid; methacrylphenyliminodiacetic acid; acrylamidophenyliminodiacetic acid; and methacrylamidophenyliminodiaceticdiacetic acid; N,N-(carboxymethyl,2-carboxyallyl)aniline; N,N-bis(2-carboxyallyl)aniline; m- or p- vinyl, m- or p- benzyl-N-phenyliminodiacetic acid; N,N,N',N'-p-phenylenediaminotetraacetic acid; N,N'-[1,2-ethanediyl bis(oxy-2,1-phenylene)-bis N-carboxymethyl] (also known as 1,2-bis(o-aminophenoxy-)ethane-N,N,N',N'-tetraacetic acid or BAPTA); o-,m-and p-biphenylenediiminodiacetic acid; and carboxy-N-phenyliminodiacetic acid.

N-phenyliminodiacetic acid (PIDAA) and related N-substituted iminodiacetic acids as well as their salts are unique in their ability to chelate metal cations such as calcium. Because the moderate acidity of PIDAA ($pK_1$=2.4) and excellent chelating potential, when dissolved in an aqueous solvent, a polar solvent, or an aqueous polar solvent, particularly in aqueous acetone, this compound has excellent chelating potential and is capable of effectively modifying the smear layer of cut and ground dentin surfaces by a single application without a subsequent aqueous wash step.

Figure 2:
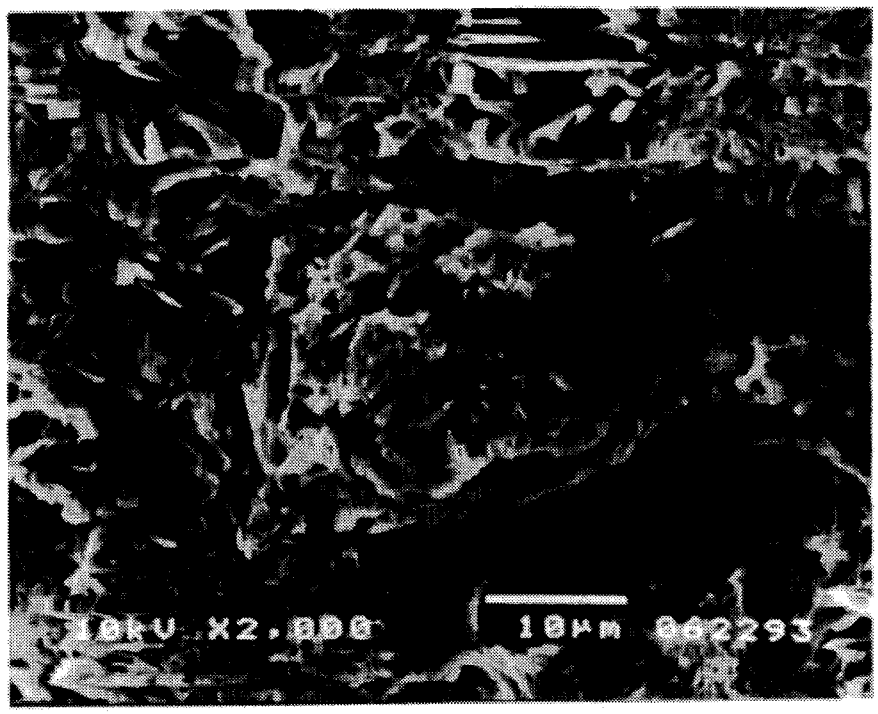
FIG. 2 is a scanning electron photomicrograph of dentin at a magnification of 2,000X after treatment with a solution of 0.3M NPG in acetone/water.
Figure 3:
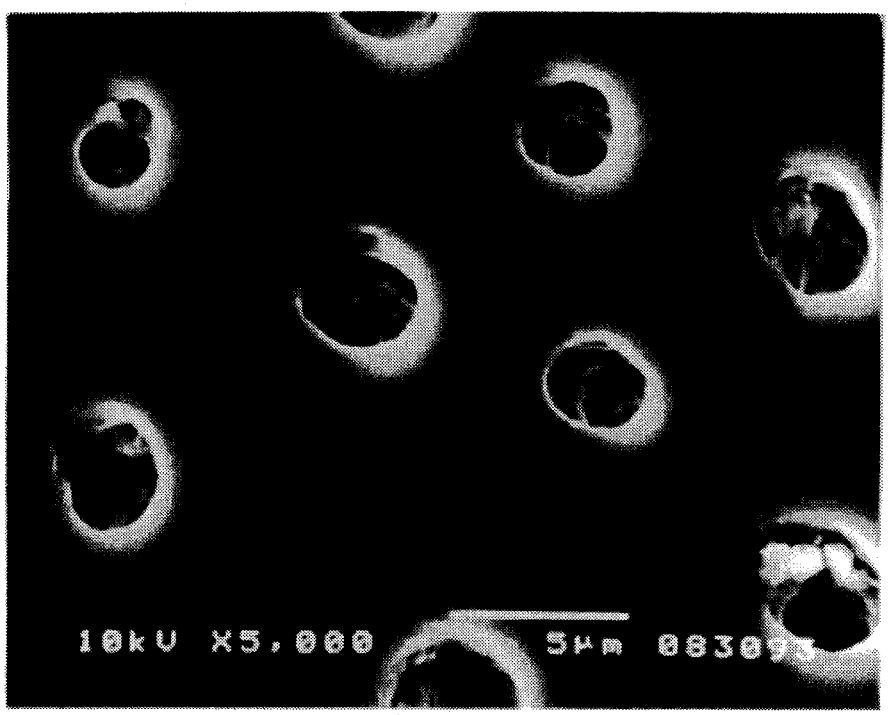
FIG. 3 is a scanning electron photomicrograph of dentin at a magnification of 5,000X after treatment with a 0.3M solution of N-phenyliminodiacetic acid (PIDAA) in acetone/water.

The surface morphology of cut and ground dentin after various pretreatments was examined by scanning electron photomicrographs. The results thereof, shown in FIGS. 1 to 3, illustrate the superior results obtained by the present invention. Thus, FIG. 1 is a scanning electron photomicrograph at a magnification of 3,000X of a freshly cut dentin surface after rinsing with water. This photomicrograph shows the untreated original smear layer. FIG. 2 is a scanning electron photomicrograph at a magnification of 2,000X of a cut dentin surface after treatment with 0.3M N-phenylglycine (NPG), an excellent primer currently being used in dental applications, dissolved in acetone/water (1:1, v/v). These two scanning electron photomicrographs may be compared with that of FIG. 3 which is a photomicrograph of a cut dentin surface treated with a solution of 0.3M PIDAA dissolved in acetone/water (1:1, v/v) at a magnification of 5,000X. These scanning electron photomicrographs also revealed that the dentinal tubules were obturated with debris. This obturation may reduce pulp sensitivity and the flow of dental fluids to the bonded interface. Thus, treatment of dentin with PIDAA followed by PMDM resulted in excellent composite-to-dentin bonds in a 2-step procedure.

These results demonstrate the superior effectiveness of PIDAA in the appropriate solvent system to function as both an etchant and a primer, thereby providing a simplified technique for effective bonding to dentin. Because of its moderate acidity (compared to nitric, maleic and phosphoric acids, for example) less subsurface damage occurs in the conditioned dentin. Furthermore, etching with PIDAA does not require a rinsing step and in many instances it is preferred that such a step not be used.

Many of the compounds used in the combined etchant/primer compositions of the present invention are available from commercial sources. Where unavailable commercially, the synthesis of appropriate compounds is not particularly complicated. Thus, the compounds in which $R^1$ is an aromatic group, such as a phenyl or substituted phenyl group may be prepared as described by Lin et al., *Synthesis*, 7, 548–549 (July 1989). This method involves reacting the appropriate substituted or unsubstituted aniline with sodium chloroacetate in the presence of n-butyllithium as a base. Many of the compounds according to formula (I) in which R= $R^2$ may be prepared in a similar manner Many of the olefinic compounds in which R=$R^2$ may be prepared by a method similar to that used to prepare the crotonyl-N-iminodiacetic acid compounds. For example, 3-aminocrotonic acid and its esters can be reacted with haloacetic acid or derivatives thereof, such as chloroacetic acid, to synthesize the analogous N,N-diacetic acid derivatives of crotonic acid, its esters, salts, etc., using a mild base in an appropriate solvent. Alternatively, the aromatic or appropriate aliphatic amine may be reacted with a haloacetic acid or a derivative thereof. In addition, iminodiacetic acid may be reacted with the appropriate conjugated organic halide in an appropriate solvent and in the presence of a base such as triethylamine.

Solvent Systems

The etchant/primer compositions of the present invention include not only a suitable etchant/primer compound but also a suitable solvent. Such a solvent system includes water and/or a polar solvent which is partially or totally soluble in water. For dental applications, a suitable solvent system is one which completely wets and diffuses into the conditioned surface of enamel, and particularly dentin, in a clinically acceptable period of time (on the order of about 15 to about 180 seconds). As used here, "conditioned" refers to altering the smear layer and the underlying dentin surface to a depth of not more than about 5 microns. Such a solvent may be water or a polar solvent preferably an aqueous polar solvent system. When used in dental applications, while the solvent system may be anhydrous before use, due to the constant presence of saliva in the oral cavity, once introduced therein, the solvent generally contains some water. Preferred organic solvents include low molecular weight ketones, such as acetone and methyl ethyl ketone, which are readily soluble in water over a wide concentration range, or a low molecular weight alcohol, such as ethanol or propanol. Aqueous solutions of ethylenically unsaturated monomers may also be employed as the solvent system. Exemplary of such monomers are hydroxyethyl and hydroxypropyl methacrylates and glyceryl mono- and dimethacrylates. Each of these monomers has at least one hydroxyl group per molecule. Other solvents include polar aprotic liquids such as dimethylformamide, dimethylacetamide and dimethylsulfoxide. Water and a mixed solvent system of water and acetone are preferred. In such a solvent system, the amount, by volume, of acetone may range from about 5 to about 90% acetone, with the remainder being water. Preferred is a 1:1 mixture of acetone and water.

Water may be used more frequently as the solvent when the etchant/primer compound is a water-soluble salt.

The solvent serves the purpose of assuring that the etchant/primer compound contacts all exposed dentin surfaces so that the etchant/primer compound can function successfully. Thus, the solvent system must appropriately reduce the viscosity of the etchant/primer compound as well as provide a suitable surface tension such that the composition may penetrate the smallest cracks, fissures or pores in the dentin surface to assure suitable contact of the polymerized adhesive component with the dentin. Although not necessary in every instance, it is preferred that the solvent be volatile at body temperature. In some instances, to provide the appropriate surface tension, a surfactant may be employed. In most instances, as when the etchant/primer compound is combined with an adhesive monomer system, it is preferred that the solvent system used to dissolve the etchant/primer compound also be miscible with the solvent system employed to dissolve the adhesive monomer system and/or be capable of dissolving the adhesive monomer system itself.

The concentration of the etchant/primer compound in the solvent system varies over a large range, depending upon the solubility of the etchant/primer compound in the solvent system. Accordingly, this will depend on the particular etchant/primer compound and solvent system selected. When the preferred compound is PIDAA and the preferred solvent system of acetone/water are employed, typically the concentration ranges from about 1 to about 20%, by weight, based on the total weight of the composition.

Etchant/Primer/Adhesive Systems

The etchant/primer compositions which include an etchant/primer compound and an appropriate solvent system may be used with an appropriate adhesive monomer system in either a 1 or 2 step procedure in what may be considered an etchant/primer/adhesive monomer system. Thus, in a 2-step procedure, the etchant/primer composition is applied to the dentin surface by a conventional technique used to apply currently used etchants or primer compositions, either with or without rinsing thereafter. An adhesive monomer system may be applied in a second step thereafter using a conventional technique. Alternatively, the adhesive monomer system may be combined with the etchant/primer composition of the present invention and the combined solution of etchant/primer compound, solvent system and adhesive monomer system may be applied to the dentin surface in a single step by a currently used technique. In such a situation, the adhesive monomer compound may be simply added and dissolved in the etchant/primer composition, which contains a solvent suitable for dissolving the adhesive monomer system or the etchant/primer compound may be added to a composition of the adhesive monomer system and solvent which is also appropriate to dissolve the etchant/primer compound. Alternatively, the two compositions, each employing a solvent, may be combined where the solvent system is the same for each composition or one solvent is miscible with the other without precipitation of any of the dissolved solutes.

Etchant/Primer Compositions

The etchant/primer compositions used in the etchant/primer/adhesive systems of the present invention include those etchant/primer compositions discussed above. The primary consideration in selecting such etchant/primer composition is that the composition be compatible with the adhesive monomer system selected and/or the solvent, separate initiator (when used) and solvent employed with the adhesive monomer system. By "compatible" is meant that the solvents and reactants are soluble or miscible in one another and that no adverse reactions which depart from the object of the present invention occur.

Adhesive Monomer Systems

Adhesive monomer systems suitable for use in the present invention include those monomers, which when polymerized, form a polymeric matrix which includes the properties and satisfies the objects of the present invention. Such properties include a high mechanical strength of the polymeric matrix itself as well as high shear strength associated with strong anchoring to a substrate, such as dentin. In addition, where appropriate, an initiator, such as a free radical initiator, is included in the monomer system. The monomeric compounds and the polymers which they form, also known as "bonding resins" when used in dental applications, correspond in most instances to substances currently used for adhesive, restorative, sealant and related purposed. These compounds are organic monomeric compounds which include at least one unit of unsaturation, typically an ethylenic unit of unsaturation. The adhesive monomer systems of the present invention may include a single monomeric compound or a plurality thereof. In the latter instance, a second or additional compound may function as a comonomer in the formation of a copolymer and/or as a cross-linking agent to form a cross-linked polymer. Preferably, the adhesive monomer system includes at least one acrylate or methacrylate monomer, with the latter being preferred in many instances because of lower toxicity. Suitable examples of the monomer systems which may be employed in the present invention, including both monomeric compounds and, when employed, a free radical initiator, are described in the U.S. patent application filed concurrently herewith to Antonucci et al., having the title "Polymeric Amorphous Calcium Phosphate Compositions" and U.S. patent application Ser. No. 08/189,708, which is specifically incorporated herein by reference. To mention but a few examples, the bonding resins of the present invention may range from simple acrylic monomers, such as methyl methacrylate, to more complex resins, such as triethylene glycol dimethacrylate, 2-hydroxyethyl methacrylate, or Bis-GMA.

Monomeric bonding agents which are highly effective in the present invention are those that have surface-active functional groups such as carboxylic acid groups, or groups which easily hydrolyze in the presence of water to form such acidic groups, as for example the carboxylic acid anhydride group; phosphate or hydrogen phosphate groups, sulfonic acid or sulfonate groups, hydroxyl groups, aldehyde groups, isocyanate groups, secondary and tertiary amino groups and quaternary ammonium groups. Particularly preferred in the present invention is the carboxylic acid group. A monomer which is particularly preferred is PMDM. Another preferred monomer is the reaction product glyceryl dimethacrylate and pyromellitic acid dianhydride (PMGDM). Other effective adhesive monomeric systems include the combination of benzophenone tetracarboxylic acid and 2-hydroxyethyl methacrylate (HEMA), as well as those disclosed in the aforementioned patents to Bowen, incorporated herein by reference.

The iminodiacetic etchant/primer compositions of the present invention may be used with several types of bonding systems, particularly in dentin bonding applications.

The adhesive monomer systems of the present invention may also include free-radical initiator and accelerators. These may either include chemical type (redox systems) in which a peroxide initiator and a polymerization accelerator react at ambient temperatures to initiate the polymerization of the monomer system or a photoinitiator system in which light, such as ultraviolet light, but preferably the visual portion of the spectrum is employed as the energy source to stimulate free-radical initiation. Examples of such chemical initiators include hydroperoxides, peresters or diacyl peroxides, such as benzoyl peroxide. Examples of amine accelerators include tertiary aromatic amines, such as N,N-dimethyl-p-toluidine. Suitable photoinitiators include benzyl-2,3-butanedione, phenyl-1,2-propandione, and camphorquinone (CQ).

Chemical and photo-initiated bonding resins, both with and without a carboxylic acid monomer, such as PMDM, provide significant shear bond strengths between the polymeric composite and dentin. In various experiments, the highest average shear bond strength of 27±5.3 MPa was obtained with a monomer system of PMDM (10% w/w) in acetone activated with camphorquinone on a previously PIDAA treated dentin.

While such monomer systems, including both a single monomeric compound or a plurality thereof and an initiator, optionally including an activator, may be employed in the present invention, it is frequently unnecessary to include an initiator or accelerator of the type commonly used with typical adhesive monomer systems. Thus, when the iminodiacetic acids or their salts used as the etchant/primer compounds of the present invention are applied to a substrate, such as dentin, with only light rinsing or without rinsing the substrate thereafter, it is unnecessary to include a separate initiator and optional accelerator. Because of such behavior, the etchant/primer compositions of the present invention may also be combined with the adhesive monomer systems of the present invention shortly before use, and thereby used in a single component system. Such modes of use result from the fact that the etchant/primer compositions of the present invention function not only as etchants, but also as polymerization activator/co-initiators when combined with ethylenically unsaturated monomers. It is preferred to use the highly effective monomeric bonding agents with surface-active functional groups, discussed above, such as PMDM, when clinically preferred reaction rates are desired. They also behave as polymerization accelerators for certain initiators, including diacyl peroxides, such as benzoyl peroxide, and peroxyesters, such as t-butylperoxymaleic acid. The iminodiacetic acid etchant/primer compositions of the present invention are also effective as photoinitiators/co-activators with vicinal diketones, such as CQ.

While the etchant/primer/adhesive monomer systems of the present invention provide very high shear bond strengths, the mechanical strength between the etchant/primer composition treated dentin and the adhesive polymer composite formed thereafter may be further strengthened by inclusion of catalytic amounts of redox metal compounds in the system. These are typically mixed with the monomer adhesive system when later applied. Such redox metal compounds may be inorganic or organic metal compounds. Exemplary of such redox metal compounds are iron compounds in both oxidation states, such as ferrous sulfate, ferric sulfate, ferrous oxalate, ferric oxalate, ferrous and ferric chloride; copper salts, such as cuprous and cupric sulfate; titanium (III) and (IV) salts; such as titanyl acetylacetonate; cerium (III) and (IV) salts, ammonium nitrate; silver compounds such as silver nitrate, silver citrate and silver benzoate, etc.

The adhesive monomer compositions used in the present invention may be employed in the same manner as they are conventionally employed in conjunction with separate etchant and primer treatments. That is, the etchant/primer composition of the present invention may be applied to the surface of the substrate, such as a dentin surface, and either lightly rinsed with water or the rinsing step eliminated altogether. Thereafter, the adhesive monomer composition may be applied to the substrate surface which has just undergone treatment with the etchant/primer composition.

Etchant/Primer/Adhesive Monomer

Compositions and Kits

Because of the properties described above for the etchant/primer compounds of the present invention, various types of systems or kits may be used to form high shear strength bonds between a polymeric material and a substrate, particularly dentin and particularly in a dental procedure. Thus, either a one step or two step procedure may be employed using one of several two-composition systems according to the present invention. Both systems include the etchant/primer composition of the present invention, described above. The systems differ, however, in the second component and the manner in which the systems are employed.

The first system, designated as system (A), includes as a first component, an etchant/primer composition (A1), which may be placed in a separate container or separately packaged or at least maintained separate from the second composition until it is ready to be used. The second component of etchant/primer/adhesive monomer system (A) corresponds to an adhesive monomer system (A2) described above, which includes not only one or more monomeric compounds, but also an initiator and optionally an activator. Like the first component of system (A), (A1), the adhesive monomer composition may be preferably separately packaged or at least kept separate from the etchant/primer compound or composition that corresponds to the first component (A1) until it is to be used.

The etchant/primer/adhesive monomer system (A) of the present invention may be used as described above. That is, a suitable amount of etchant/primer composition (A1) may be removed from its container and applied to the substrate surface and allowed to remain for a period of about 15 to about 180 seconds. Thereafter, either with light rinsing with water or without any rinsing, a suitable amount of the solution of adhesive monomer composition (A2) to form a polymeric matrix and anchor to the substrate, may be removed from its container and applied to the etchant/primer treated substrate. Due to the function of the initiator, the subsequently applied adhesive monomer system will cure and form mechanically strong bonds to the substrate surface.

The second etchant/primer/adhesive monomer system (B), like the aforementioned system (A), includes an etchant/primer composition (B1) as a first component which is, in most instances, the same or substantially the same as the etchant/primer composition (A1) of the system (A) described above. The most significant difference between the two systems is in the second component, the adhesive monomer component or composition (B2). The adhesive monomer composition (B2) of the second etchant/primer/adhesive monomer system (B) differs from (A2) in that it contains a monomer system without the conventional free-radical initiator and may also include no accelerator, other than those discussed below. Like the etchant/primer/adhesive monomer system (A), the system (B) may employ separately packaged (i.e., in separate containers) components (B1) and (B2). The components (B1) and (B2) may each contain their own solvent systems, which are the same or are miscible with one another and compatible with the separate solutes. Where only one of the components, the etchant/primer compound(s) or the adhesive monomer(s) is dissolved in a solvent system, the solvent should be one suitable for dissolving the other components of the system.

In use, the (B) system may be used according to one of two different methods according to the present invention. Thus, the first method is identical to the method employed with the (A) system. That is, a solution of (B1) is applied to the substrate, typically dentin, and either lightly rinsed with water or left unrinsed. Thereafter, a solution of the adhesive monomer (B2) is applied to the substrate surface and polymerization and curing allowed to take place. Because of the initiating and accelerating properties of the etchant/primer compositions of the present invention, the absence of an initiator in (B2) presents no problem in rapid polymerization, particularly when highly active monomers of the type discussed above, such as those which include acid, hydroxyl, amine or quaternary ammonium groups are used, or when an activating cation is present.

In the second method of using the etchant/primer/adhesive monomer systems (B), the steps of etching, priming and forming an adhesive polymer may be accomplished in a single step. Thus, the separate components (B1) and (B2), including the substances described above, may be combined in a single solution and applied to the substrate. In this method, rather than sequentially applying separate solutions, a single solution containing the etchant/primer compound and the solvent system of the present invention as well as the monomer system, and generally without a conventional free-radical initiator, is applied as a single solution. In such an instance, either (B1) or (B2) may be solvent-free, with the other of the components containing a solvent system suitable for dissolving the solvent-free component. Alternatively, both components may include a suitable solvent system which is compatible with the solvent system of the other component.

What is claimed is:

1. An etchant/primer/adhesive monomer composition comprising:

a compound having the formula

wherein $R=R^1$ or $R^2$;

$R^1$=an aromatic group;

$R^2$=a conjugated aliphatic group;

Y=a single bond, $CH_2$, $CHCH_3$ or $C=CH_2$; and each M is independently H, an alkali metal, an alkaline earth metal, aluminum, a transition or redox metal or an alkyl group having 1 to 18 carbon atoms, with the proviso that when both M groups are alkyl groups, the compound corresponding to formula I be capable of being easily hydrolyzed, displaced, or exchanged with other reagents present in the etchant/primer composition;

a polar solvent; and an adhesive monomer system.

2. An etchant/primer/adhesive monomer composition according to claim 1 wherein said polar solvent system comprises an aqueous solvent.

3. An etchant/primer/adhesive monomer composition according to claim 2 wherein said aqueous solvent system comprises water and acetone.

4. An etchant/primer/adhesive monomer composition according to claim 1 wherein $R^1$ comprises $C_6H_5$ or $C_6H_4R^3$, and wherein $R^3=N(CH_2CO_2M)_2$; $C_6H_4N(CH_2CO_2M)_2$; $O(CH_2)_2OC_6H_4N(CH_2CO_2M)_2$; $CH=CH_2$; $CO_2H$; F; Cl; Br; I; OH; SH; (m- or p-) $CH_2C_6H_4$(m- or p-) $CH=CH_2$; $OCOC(R^4)=CH_2$; $NR^4COC(R^4)=CH_2$; $(CH_2)_2OCOC(R^4)=CH_2$; $C_6H_5$; an alkyl group having 1 to 12 carbon atoms; $HOCH_2$; $HOCH_2CH_2$; $R^5{}_2N$; $R^6O$; $R^6S$; $R^6CO$; $R^7CONH$; $R^7COCO$, wherein $R^4$=H or $CH_3$;

wherein $R^5$=H or an alkyl group having 1 to 8 carbon atoms;

wherein $R^6$=an alkyl group having from 1 to 6 carbon atoms; and wherein $R^7$=an alkyl group having 1 to 6 carbon atoms.

5. An etchant/primer adhesive monomer composition according to claim 1 wherein said compound of formula (I) is phenyliminodiacetic acid, salts thereof or esters thereof.

6. An etchant/primer adhesive monomer composition according to claim 1 wherein $R^2$ comprises a residue of crotonic acid, salts thereof or esters thereof.

7. An etchant/primer adhesive monomer composition according to claim 1 wherein said adhesive monomer system includes at least one monomer with an ethylenically unsaturated group and having at least one surface-active functional group.

8. An etchant/primer adhesive monomer composition according to claim 7 wherein said at least one surface-active functional group is selected from the group consisting of carboxylic acid; phosphate, hydrogen phosphate, sulfonic acid, sulfonate, hydroxyl, aldehyde, isocyanate, secondary and tertiary amino; and quaternary ammonium groups; and groups which hydrolyze to form carboxylic acid groups.

9. An etchant/primer adhesive monomer composition according to claim 1 wherein said adhesive monomer system includes the reaction product of hydroxyethyl methacrylate and pyromellitic acid dianhydride.

10. An etchant/primer adhesive monomer composition according to claim 1 wherein said adhesive monomer system includes a free radical initiator.

11. An etchant/primer adhesive monomer composition according to claim 1 wherein said adhesive monomer system includes a redox metal compound.

12. An etchant/primer/adhesive monomer composition according to claim 2 wherein said solvent includes an alcohol.

13. An etchant/primer/adhesive monomer composition according to claim 2 wherein said solvent includes ethanol.

14. An etchant/primer/adhesive monomer composition according to claim 2 wherein said solvent includes dimethylsulfoxide.

15. A kit for forming a polymeric material at and a strong integrated bond with a dental or other substrate surface comprising:

(a) a first container containing an etchant/primer composition comprising:

a compound having the formula

wherein $R=R^1$ or $R^2$;

$R^1$=an aromatic group;

$R^2$=a conjugated aliphatic group;

Y=a single bond, $CH_2$, $CHCH_3$ or $C=CH_2$; and each M is independently H, an alkali metal, an alkaline earth metal, aluminum, a transition or redox metal or an alkyl group having 1 to 18 carbon atoms, with the proviso that when both M groups are alkyl groups, the compound corresponding to formula I be capable of being easily hydrolyzed, displaced, or exchanged with other reagents present in the etchant/primer composition;

(b) a second container containing an adhesive monomer system; and (c) at least one polar solvent system included in at least one of (a) and (b).

16. A kit according to claim 15 wherein said kit is free of any compound capable of functioning as a free radical initiator other than said etchant primer compound.

17. An etchant/primer/adhesive monomer composition comprising:

a compound having the formula $$RN(CH_2YCO_2M)_2 \quad \quad I$$

wherein R=$R^1$ or $R^2$;

$R^1$=an aromatic group;

$R^2$=a conjugated aliphatic group;

Y=a single bond, $CH_2$, $CHCH_3$ or $C\ominus CH_2$; and each M is independently H, an alkali metal, an alkaline earth metal, aluminum, a transition or redox metal or an alkyl group having 1 to 18 carbon atoms, with the proviso that when both M groups are alkyl groups, the compounds corresponding to formula (I) be capable of being easily hydrolyzed, displaced, or exchanged with other reagents present in the etchant/primer composition;

a polar solvent; and an acrylic adhesive monomer system

18. An etchant/primer/adhesive monomer composition according to claim 17 wherein said polar solvent system comprises an aqueous solvent.

19. An etchant/primer/adhesive monomer composition according to claim 18 wherein said aqueous solvent system comprises water and acetone.

20. An etchant/primer/adhesive monomer composition according to claim 17 wherein $R^1$ comprises $C_6H_5$ or $C_6H_4R^3$, and wherein $R^3$=$N(CH_2CO_2M)_2$; $C_6H_4N(CH_2CO_2M)_2$; $O(CH_2)_2OC_6H_4N(CH_2CO_2M)_2$; $CH=CH_2$; $CO_2H$; F; Cl; Br; I; OH; SH; (m- or p-) $CH_2C_6H_4$ (m- or p-) $CH=CH_2$; $OCOC(R^4)=CH_2$; $NR4COC(R^4)=CH_2$; $(CH_2)_2OCOC(R^4)=CH_2$; $C_6H_5$; an alkyl group having 1 to 12 carbon atoms; $HOCH_2$; $HOCH_2CH_2$; $R^5_2N$; $R^6O$; $R^6S$; $R^6CO$; $R^7CONH$; $R^7COCO$;

wherein $R^4$=H or $CH_3$;

wherein $R^5$=H or an alkyl group having from 1 to 8 carbon atoms;

wherein $R^6$=an alkyl group having from 1 to 6 carbon atoms; and wherein $R^7$=an alkyl group having 1 to 6 carbon atoms.

21. An etchant/primer/adhesive monomer composition according to claim 17 wherein said compound of formula (I) is phenyliminodiacetic acid, salts thereof or esters thereof.

22. An etchant/primer/adhesive monomer composition according to claim 17 wherein $R^2$ comprises a residue of crotonic acid, salts thereof or esters thereof.

23. An etchant/primer/adhesive monomer composition according to claim 17 wherein said solvent includes alcohol.

24. An etchant/primer/adhesive monomer composition according to claim 17 wherein said solvent includes ethanol.

25. An etchant/primer/adhesive monomer composition according to claim 17 wherein said solvent includes dimethylsulfoxide.

* * * * *